United States Patent [19]

Sachdeva et al.

[11] Patent Number: 5,232,361
[45] Date of Patent: Aug. 3, 1993

[54] ORTHODONTIC BRACKET

[76] Inventors: Rohit C. L. Sachdeva, 2605 Courtside La., Plano, Tex. 75093; Yoshiki Oshida, 310 Haddonfield Dr., DeWitt, N.Y. 13214

[21] Appl. No.: 864,396

[22] Filed: Apr. 6, 1992

[51] Int. Cl.[5] .............................................. A61C 7/00
[52] U.S. Cl. ............................................ 433/8; 433/9
[58] Field of Search ....................................... 433/8, 9

[56] References Cited

U.S. PATENT DOCUMENTS

| | | | |
|---|---|---|---|
| 4,197,643 | 4/1980 | Burstone et al. | 433/20 |
| 4,536,154 | 8/1985 | Garton et al. | 433/8 |
| 4,626,209 | 12/1986 | Tsai et al. | 433/9 |
| 4,659,309 | 4/1987 | Merkel | 433/9 |
| 4,717,341 | 1/1988 | Goldberg et al. | 433/9 |
| 4,842,513 | 6/1989 | Haarmann | 433/8 X |
| 4,889,485 | 12/1989 | Iida | 433/9 |
| 4,902,224 | 2/1990 | Collins et al. | 433/8 |
| 4,915,625 | 4/1990 | Tsukuma et al. | 433/8 |
| 4,927,361 | 5/1990 | Smith et al. | 433/9 |
| 4,954,080 | 9/1990 | Kelly et al. | 433/8 |
| 5,011,403 | 4/1991 | Sadoun et al. | 433/8 |
| 5,011,410 | 4/1991 | Culler et al. | 433/208 |
| 5,032,081 | 7/1991 | Farzia-Nia et al. | 433/8 |
| 5,071,344 | 12/1991 | Wong et al. | 433/8 |
| 5,078,596 | 1/1992 | Carberry et al. | 433/8 |
| 5,110,290 | 5/1992 | Wong | 433/9 |

OTHER PUBLICATIONS

G. V. Newman "Adhesion and orthodontic plastic attachments" 1969 (Dec.) vol. 56, pp. 583–584.
G. E. Scott "Fractive Toughness and Surface Cracks" 1988 (Jan.) vol. 58 pp. 6–8.
M. L. Swarz "Ceramic Brackets" 1988 (Feb.) vol. 22, pp. 86–87.
V. P. Joseph et al. "The Shearbond Strengths of Stainless Steel and Ceramic Brackets Used with Chemically and light-actuated Composite Resins" 1990 (Feb.) vol. 97, pp. 121–123.
R. Maijer et al. "Corosion of Orthodontic Bracket Bases" 1982 (Jan.) vol. 81, pp. 44–46.
W. R. Schriver et al. "Allergic Response to Stainless Steel Wire" 1976 (Nov.), vol. 42 pp. 579–580.
A. Schroeder et al. "The Reactions of Bone, Connective Tissues, and Epithelium to EndoSteel Implants with Titanium-Sprayed Surfaces" 1981, vol. 9 pp. 23–25.
R. P. Kusy et al. "Coefficients of Friction for Arch Wires in Stainless Steel and Polycrystaline Alumina Bracket Slots" 1990 (Oct.) vol. 98 pp. 303–306.
D. H. Pratten et al. "Fractional Resistance of Ceramic and Stainless Steel Orthodontic Brackets" 1990 (Nov.) vol. 98, pp. 399–400.

Primary Examiner—Robert P. Swiatek
Assistant Examiner—Nicholas D. Lucchesi
Attorney, Agent, or Firm—Wall and Roehrig

[57] ABSTRACT

By using titanium, titanium based alloys, or related metals or alloys, an orthodontic bracket can be manufactured which is lighter and stronger than any conventional type of bracket made of stainless steels, plastics and even ceramics. Ti based brackets have shown excellent corrosion resistance and possess good biocompatibility. Surface treatments including nitriding, diamond coating, pre-oxidation or shot-peening on the slot bottom surface of such brackets reduce the friction coefficient against the orthodontic archwire. Furthermore, the bonding strength may be enhanced by shot-peening, ion beam etching or reactive ion etching on the tooth contact surface of the base portion of the bracket.

20 Claims, 1 Drawing Sheet

ORTHODONTIC BRACKET

DESCRIPTION

This invention relates in general to a dental appliance, and more specifically an orthodontic bracket that has excellent corrosion resistance, very good biocompatibility in that it minimizes the risk of an allergic reaction in patients, substantially greater spring back properties, properties that make chemical bonding to the present orthodontic adhesives possible, a low coefficient of friction particularly in the slot area of the bracket, and high ratio of relative strength and stiffness to weight.

BACKGROUND OF THE INVENTION

Orthodontic appliances can generally be divided into two groups: "reactive" and "active". Traditionally, appliances such as brackets have been considered "reactive" appliances since their only purpose has been to physically hold in place a force generating "active" appliance such as an archwire. It is the recovery force of the archwire which results in tooth movement.

Orthodontic brackets have manufactured from materials such as stainless steel as disclosed in U.S. Pat. Nos. 4,536,154 and 4,659,309; ceramics as disclosed in U.S. Pat. Nos. 4,954,080, 5,011,403, and 5,071,344; certain types of plastics as disclosed in U.S. Pat. No. 4,536,154; or plastic composites as disclosed in U.S. Pat. No. 5,078,596.

Brackets made of ceramics or various types of stainless steels are generally rigid and strong. On the other hand, plastic materials, due to their relatively lower strength, exhibit permanent deformation during treatment. This failure is propagated by the stresses generated by the loading forces generated by "active" elements such as an archwire as well as by masticatory forces.

Brackets fabricated from polycarbonate demonstrate distortion under torsional loading generated by orthodontic archwires, and also possess a high propensity for water absorption, which may result in discoloration of the bracket and undesired staining (G. V. Newman, Am J. Orthod. 1969;56:573-588). These factors limit the use of such brackets in the oral environment.

Ceramic brackets are extremely brittle and even the smallest surface cracks (flaws) can dramatically reduce the load required for fracture (G. E. Scott, The Angle Orthodontist, 1988;58:5-8). Brackets that distort or fail during treatment render tooth movement ineffective and minimize control of tooth movement, thereby extending treatment time. Chemical retention of the ceramic bracket base to adhesive is generally facilitated by a coating of silica and silane coupling agent. The resultant chemical bond is very strong and may cause the enamel adhesive interface to be stressed during either debonding or sudden occlusal force. Hence, irreversible damage to the enamel of the entire tooth may occur and is particularly significant when bonding endodontically treated teeth or teeth with large restorations. (M. Schwartz, J. Clinical Orthod 1988;22:82-88). In addition, due to the hardness of ceramic brackets, abrasion during the chewing process can lead to enamel wear.

It has been suggested that adequate bond strengths for brackets should be in the vicinity of 5.9 to 7.8 MN/m$^2$. With ceramics, bond strengths as high as 28.27 MN/m$^2$ may be obtained which may compromise the safety margin of the stresses that can be withstood by the cohesive strength of enamel (V. P. Joseph et al., Am J Orthod, 1990;97:121-125). This may lead to enamel fracture. The incidence of fracture of ceramic brackets themselves is also of concern. It has also been reported to be as high as 6.66% (VPJ, ibid.). Pieces of bracket may be ingested or inhaled inadvertently if fracture occurs in the mouth during treatment.

On the other hand, it appears that stainless steel brackets begin to deform when shearing forces are applied. This leads to debonding of the bracket before reaching the cohesive fracture strength of the adhesive. This phenomenon prevents any enamel or bracket fracture. Steel failure, which can lead to bracket deformation or even breakage, has not been considered as dramatic.

While the mechanical strength of a bracket is an important design consideration, its corrosion resistance is equally important. This characteristic determines its biodegradation and the leaching of potentially harmful ions into the oral environment. Therefore the choice of a material that demonstrates high corrosion resistance while being biocompatible is vital for use in the oral environment.

In the process of bonding a bracket to them, teeth are conventionally treated by an acid-etch technique with subsequent placement of the orthodontic bracket. When using 304 stainless steel brackets, it was reported that the presence of voids together with poor oral hygiene led to crevice corrosion of 304 stainless steel and formation of colored corrosion products that resulted in enamel stains (R. Maijer et al., Am J. Orthod, 1982;81:43-48).

Both enamel staining, and the most serious problem of mucosal allergy, also due to the heavy metals leaked from corroded appliances, are phenomena which are often encountered and have been comprehensively studied. What makes the problem more dramatic is the fact that nickel, found in all the stainless steels used in orthodontics, produces more allergic reactions than all other metals combined; furthermore this ion is cytotoxic. Delayed hypersensitivity response to nickel containing stainless steel (e.g., AISI 304 and 316 stainless steel) has been reported (W. R. Schriver et al., Oral Surg, 1976;42: 578-581).

On the other hand, titanium and titanium based alloys are reported to have the greatest corrosion resistance of any known metallic materials. Implants in monkeys of commercially pure titanium (at least 99% titanium by weight), show no evidence of corrosion or release of Ti in adjacent tissues after being as much as 1 ½ years (A. Schroeder et al., J Max-ac Surg 1981;9: 15-25). This is due to a more stable passive (oxide) films formed on Ti and Ti-based alloys. Related metals such as Cr and Co, and alloys of Cr and Co as well as alloys of Zr, Si, B, Be and Nb should offer advantages similar to that of Ti and its alloys.

Frictional resistance is another important design consideration of an orthodontic bracket. Translational tooth movement along an archwire requires sufficient force to overcome frictional forces between the bracket and archwire. Both the static and kinetic frictional forces generated between brackets and archwires during sliding mechanics should be minimized to allow optimal tooth movement during orthodontic mechanotherapy.

It is reported that the coefficient of kinetic friction for stainless steel (0.139) was less than that for the polycrystalline alumina bracket (0.174), with both measurements taken against stainless steel archwire (R. P. Kusy et al., Am J Orthod Dentofac Orthop, 1990;98:300–312). Although this ranking holds for both dry (air) and wet (artificial saliva solution) conditions, the coefficients of friction in wet environments generally show lower values than those in dry environments because the saliva serves itself as a lubricant (D. H. Pratten et al., Am J Orthod Dentofac Orthop, 1990;98: 398–403).

Moreover, when a stainless steel bracket was coupled with different types of archwire materials, the coefficients of kinetic friction ranged from stainless steel (lowest), to CoCr, TiNi, and β-Ti (highest), regardless of bracket product or slot size and were 0.140, 0.163, 0.337 and 0.357, respectively (R. P. Kusy et al., Am J Orhtod Dentofac Orthop, 1990;98:300–312).

Therefore, it is desirable to provide an orthodontic bracket made from material(s) having excellent corrosion resistance and biocompatibility, low coefficient of friction, high value of strength to-weight ratio, and good bonding characteristics. It is also desirable to be able to simplify the design of orthodontic brackets by constructing them as a single piece.

An additional consideration is the role of orthodontic brackets when a patient is subjected to medical imaging techniques. Among adult patients wearing orthodontic brackets, 20–25% of the population may require surgery of some sort during the course of orthodontic treatment. Metals, particularly those that contain iron, are magnetic and are referred to as ferromagnetic materials. When brackets are comprised of such ferromagnetic materials, they interfere with MRI and CT imaging by creating scatter. Ti, particularly anodized Ti, is non-magnetic and thus would limit interference on the recorded image, thereby enhancing the reliability of such diagnostic images. Ti and its alloys, as well as Cr, Co and alloys of Cr, Co, Zr, Si, B, Be and Nb all should demonstrate these desired features. Ti performs advantageously in a range from 45 to over 99% (the latter being "commercially pure" titanium). Performance increases the higher the percentage of Ti in the alloy.

OBJECTS AND SUMMARY OF THE INVENTION

It is an object of the present invention to provide an orthodontic bracket with high strength and high springback capability which can relatively readily deform elastically or superelastically (pseudoelastically) to more easily accommodate functional appliances such as orthodontic archwires with large cross sections.

It is a further object of the present invention to provide a bracket demonstrating excellent corrosion resistance and biocompatibility.

It is still another object of the present invention to provide a slot surface with low coefficient of friction by mechanical and/or chemi-physical treatments.

It is yet a further object of the invention to provide a bracket whose base portion has the ability to bond chemically to dental enamel with adequate strength so that a new bracket can be manufactured in one piece without the necessity for the addition of a mechanical interlocking system to the base.

BRIEF DESCRIPTION OF THE DRAWINGS

The above and many other objects, features and advantages of this invention will be more fully understood from the ensuing detailed description of the preferred embodiment of the invention, which should be read in conjunction with the accompanying drawings wherein.

DETAILED DESCRIPTION OF THE INVENTION

In the preferred embodiment of the present invention, a bracket was made of commercially pure titanium; said bracket having a base portion and at least one pair of tie wings. It was a cast Ti bracket.

Figure 1:
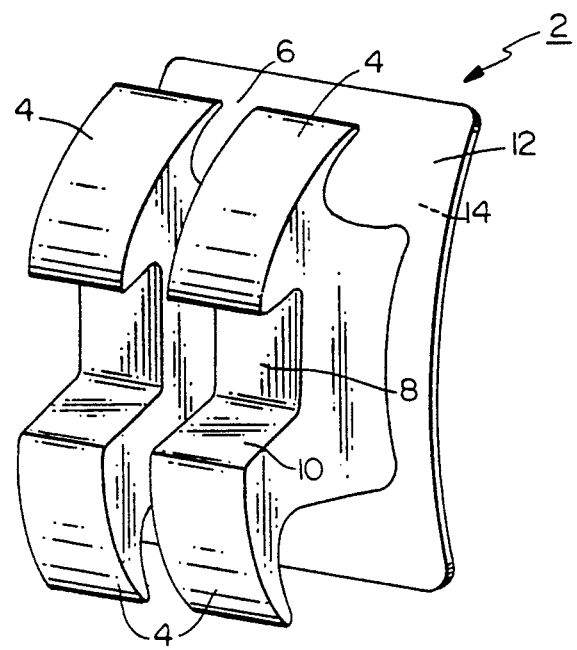
FIG. 1 is a front perspective view of an orthodontic bracket according to the present invention.
Figure 2:
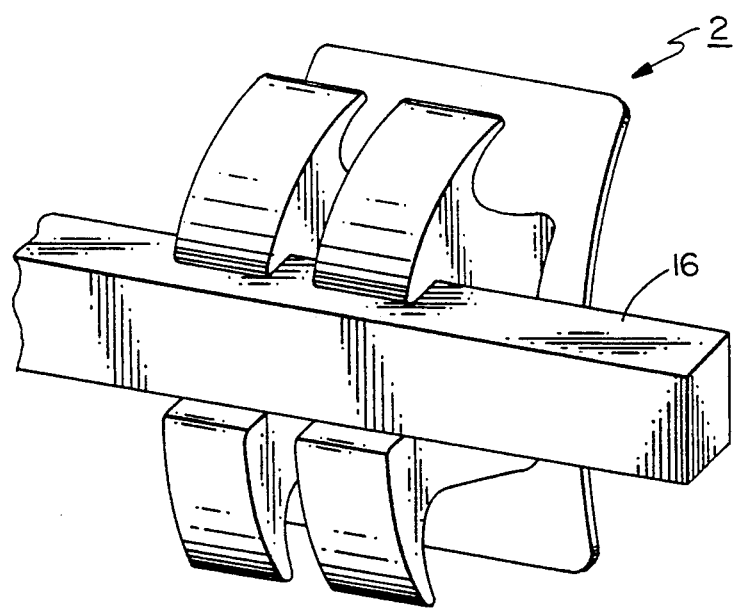
FIG. 2 is a front perspective view of an orthodontic bracket as in FIG. 1, coupled to an orthodontic archwire.

Referring to now FIG. 1, there is shown a bracket 2 having a pair of spaced apart tie wings 4 extending outwardly from a base portion 12. The space between the tie wings is a cross cut portion 6. One tie wing is the mesial tie wing having gingival and occlusal sides, and the other is the distal tie wing having gingival and occlusal sides. A pair of archwire slots are defined as openings between the gingival and occlusal sides of each tie wing 4; each slot has a bottom potion 10. The base portion 12 has two side faces, with the tie wings formed on a convex surface side, while a rear concave surface side or a tooth contact surface 14 is designed to be bonded to a dental enamel surface with an appropriate bonding chemical.

To such structured bracket 2 serving as a reactive (fixed) appliance, an orthodontic archwire (with either round or rectangular cross section and made of either stainless steels, titanium alloys, or titanium-nickel alloy) is inserted into a slot opening portion 8, serving as an active (functional) appliance to provide directional forces resulting in tooth movement.

In another embodiment of this invention, the bracket was cast from commercially pure titanium (purity is >99.9%) into a phosphate bonded investment with alumina. The mixing ratio of alumina was 10% fraction by weight of the mixed molding materials. Casting of pure titanium was done under a normal vacuum casting to produce a one piece bracket with each component as mentioned below, as seen in FIG. 1. Although in this example the titanium bracket was manufactured by a casting technique, it can be fabricated by different forming technologies; for a component such as this miniaturized piece, solid state superplastic forming is particularly suitable. Starting material for the superplastic forming is not limited to a wrought material, but may consist of a powder sintered by superplasticity, a similar technology also known as the HIP (hot isostatic pressing) process. The material for a bracket is also not limited to commercially pure titanium, but may comprise any titanium based alloy including Ti-6Al-4V, Ti-5Al-2.5Fe, Ti-4.5Al-3V-2Fe-2Mo, Ti-Ni or the like.

Ti or Ti-based brackets may alternatively be manufactured by a micro-machining as in the second embodiment of this invention, or by advanced laser machining.

Table I compares the shear and tensile bonding strengths of another embodiment of the titanium bracket of the present invention, this one having a flat rear surface and requiring no additional structures such as mesh on the tooth contact surface, with stainless steel brackets with and without mesh. Table I shows that the shear bonding strength of the Ti bracket was 7.70 $Mn/m^2$ which is equivalent to that of the stainless steel bracket with mesh on the rear side. Although the bonding strengths of these two brackets types satisfy the suggested bonding strength of 6 to 8 $MN/m^2$, it is notable that the bracket made of titanium can achieve the same level of bonding strength without any additional treatment such as placement of mesh on the tooth contact surface of the bracket.

| BRACKET TYPE AND MATERIAL | BOND STRENGTH (MN/m$^2$) | |
|---|---|---|
| | shear strength | tensile strength |
| stainless steel bracket with mesh | 7.85 | 5.40 |
| stainless steel bracket without mesh | <1.0 | <0.5 |
| titanium base bracket without mesh | 7.70 | 4.12 |

Nevertheless, if necessary, the tooth contact surface of the titanium base bracket can be further shot-peened to enhance the bonding strength due to the increased effective surface area, resulting in improved wettability against the bonding chemicals (Y. Oshida et al, Jour Materials Sci: Materials in Medicine, to be published, 1992).

Furthermore enhancement of adhesion of the bracket base may be achieved by creating a highly porous surface to provide good mechanical attachment. Two processes which may be used are ion beam etching and reactive ion etching. These are performed at low temperatures and, unlike sintering which is done at elevated temperatures, do not degrade the fatigue resistance of the alloys.

There are other physical methods of enhancing the bonding strength of the bracket to the tooth. One is undercutting the tooth contacting surface of the bracket in order to provide additional surface area. Another is providing the base portion of the bracket with a monolayer of substantially uniform sized particles in the range of 5 to 200 micron as disclosed in U.S. Pat. No. 5,071,344 to Wong et al.

It was also found that pre-oxidation of Ti and its alloys promote the surface wettability (YO, ibid., 1992) and reduce friction. The slot bottom surface can be further treated by nitriding to form titanium-nitride which is believed to harden the superficial surface layer so that the friction coefficients, particularly against the archwire surface should be markedly reduced. Nitriding is not the only technology available for hardening the titanium based surfaces; other methods such as a diamond coating may be used. Ion implantation has been shown to be very effective in reducing the wear of titanium based total joint replacements in the orthopaedic field. Ion implantation of the titanium with nitrogen or carbon increases the microhardness of the alloy. A three fold increase in microhardness can easily be achieved. Ion implantation increases the yield strength of the surface, minimizes the onset of plastic flow and scuffing wear, increases the resistance to galling and surface burnishing, and extends the lifetime of titanium based parts by approximately tenfold.

Other coatings that may be applied include C$_1$—C and i—BN (Ar, O, diamond like These coatings are transparent, quasi-amorphous and extremely adherent to the substrate. Ion implantation also enhances passivation and biocompatibility.

An alternative way to reduce the frictional coefficient of the slot bottom surface of the titanium based bracket is based upon shot-peening treatment, as mentioned above. The plurality of surface convex indentations generated by the shot-peening can serve as a saliva pool which, in turn, can serve as a lubricant in the bracket/archwire system in the oral environment. The shot-peened surface is also hardened, so that the mechanical strength of the bracket is enhanced.

These benefits of shot-peening cannot be applied to ceramic brackets because they are simply too brittle to withstand the shot energy. If applied to austenitic stainless steel brackets, special caution should be taken; it is believed that 300 series stainless steel will be subject to the stress induced martensitic transformation, so that uni-phase stainless steel will be changed to dual-phase (shot-peened martensite phase and un-peened austenite phase). These two phases show different electrochemical potentials, so that unexpected local corrosion due to the so called electrogalvanism can occur in a saliva electrolyte. If a certain level of stressing is superimposed onto the potential locations of the electrogalvanic corrosion's occurrence, the bracket will fail due to stress corrosion cracking. On the other hand, both commercially pure titanium and any type of titanium alloys including Ti-6Al-4V and Ti-5Al-2.5Fe alloy possess stable phases during and after shot-peening.

It may be desirable to use titanium-nickel based alloys to fabricate brackets due to their superelasticity and shape memory effect. Nickel dissolution from the substrate may be prevented by coating with titanium using ion beam dynamic mixing. Such a coating is very adherent, resistant to bending, and demonstrates improved corrosion resistance.

Titanium based alloys possess another important characteristic a high specific strength, defined as the ratio of the strength in MN/m$^2$ to the specific density in gr/cm$^3$. Lighter and stronger materials are required due to the increased demand for miniaturizing the appliance for optimal aesthetics. Another advantage of a smaller bracket is that it, in effect, increases the space between brackets, which effectively decreases the stiffness of the archwire. This, in turn, places less load on the wire and decreases the amount of pain experienced by the patient. Table II compares specific strengths of various bracket materials. As seen in Table II, titanium based materials are superior to all other types of metallic dental materials.

| | SPECIFIC STRENGTH |
|---|---|
| alumina | 500~680 |
| Co—Cr alloy | 80~90 |
| stainless steel | 100~120 |
| pure titanium | 100~150 |
| Ti based alloys | 200~280 |

Complete three dimensional control of tooth movement requires the use of rectangular wire in the brackets to achieve torque control from the onset of treatment. Current brackets made of stainless steel or ceramic brackets do not allow the use of large cross section archwire (greater than 0.17"×0.25") of stainless steel or titanium-molybdenum alloy initially in treatment, especially in torsional loading. This is partly because the stiffness of the stainless steel bracket is so great that the engagement of the orthodontic wire results in its deformation. In case of the ceramic brackets, fracture of the bracket occurs. In either of these cases the result may be extra manipulations on the patient either in replacing damaged brackets or substituting wire that is less stiff or has a smaller cross section.

The resilience of Ti and Ti based alloy brackets allow for engagement of a larger cross section of wire, thus facilitating early engagement of large cross section wires and providing better control of tooth movement from the very beginning of treatment. Brackets made of Ti or Ti based alloys are not only "reactive", but are also "active." They store some energy as a result of their elastic deformation, releasing it over time to augment tooth movement effectively.

| material | % approximate recovery after deformation |
| --- | --- |
| stainless steel | 15 |
| beta-3 titanium | 35 |
| titanium-nickel alloy | 90 |
| ceramics (general) | <15 |
| plastics (general) | <10 |

Referring to Table III, which compares the degree of deformation recovery of various materials, it can be clearly seen that the working range (in other words, degree of elasticity) of Ti and Ti based alloys is higher than the rest of the tested materials (for example, the resilience is at least 50% greater than that of stainless steel, the modulus of elasticity being between 2 million and 20 million pounds per square inch, depending upon the percentage of Ti in the alloy), suggesting that brackets composed of these materials can play a functional role in orthodontic devices. This allows early engagement of a full size wire in treatment since the slot will elastically deform to allow placement of the orthodontic archwire.

In summary, the titanium or titanium based alloy orthodontic bracket can offer a lighter and stronger, smaller, more aesthetic, fixed (reactive) appliance with excellent corrosion resistance as well as good biocompatibility. Furthermore, surface treatments such as nitriding, diamond coating or shot-peening on the slot bottom surface reduces the friction coefficient to enhance the translational tooth movement. Moreover shot-peening, ion beam etching, or reactive ion etching on the tooth contact surface of the base portion of the bracket will increase the bonding strength to the dental enamel. An added advantage is that such a bracket can serve as an active appliance.

While the invention has been explained with reference to the structure disclosed herein, it is not confined to the details as set forth, and this application is intended to cover modifications and changes as may come within the scope of the following claims.

What is claimed is:

1. An orthodontic bracket having a body portion formulated of at least one of a group comprised of alloys based on elements Ti, Zr, Si, B, Be, Cr, Nb and Co in a composition in which at least one of the elements of this group exists in the body portion in a range of between 40% and greater than 99% by weight.

2. An orthodontic bracket according to claim 1 wherein said bracket is made of a material that has a modulus of elasticity between 2 million and 20 million pounds per square inch.

3. An orthodontic bracket according to claim 1 wherein said bracket is made of a material that has a resilience of at least 50% greater than that of stainless steel.

4. An orthodontic bracket according to claim 1 wherein said bracket is made of a material that contains at least 45% metallic titanium by weight in its composition.

5. An orthodontic bracket according to claim 4 comprising a receptacle for accommodating an arch wire extending from a top side of a base portion and a tooth contact surface on a bottom side of said base portion.

6. An orthodontic bracket according to claim 5 wherein chemical adhesion properties of the tooth contact surface of the base portion to orthodontic adhesives is improved by further chemical treatment of the base portion.

7. An orthodontic bracket according to claim 5 wherein the chemical adhesion of the tooth contact surface of the base portion to orthodontic adhesives is improved further by addition of means for mechanical bonding.

8. An orthodontic bracket according to claim 5 wherein the chemical adhesion of the tooth contact surface of the base portion to orthodontic adhesives is improved further by attachment of particles to the base.

9. An orthodontic bracket according to claim 5 wherein the chemical adhesion of the tooth contact surface of the base portion to orthodontic adhesives is improved further by addition of means of attachment to alloys that are capable of chemically bonding to the adhesives.

10. An orthodontic bracket according to claim 5 wherein the bottom interior of the receptacle is nitrided to form a titanium nitride coating thereon in order to reduce a friction coefficient against the archwire, and also to provide resistance against wear, galling and corrosion.

11. An orthodontic bracket according to claim 5 wherein the bottom interior of the receptacle is diamond coated to reduce the coefficient of friction against the archwire, and also to provide resistance against wear, galling and corrosion.

12. An orthodontic bracket according to claim 5 wherein the bottom interior of the receptacle is pre-oxidized to improve the frictional property and resistances against wear and corrosion.

13. An or bracket according to claim 5 wherein the receptacle bottom portion is treated by one of the group of treatments of shot-peening, ion beam etching and reactive ion beam etching to reduce the coefficient of friction against the archwire.

14. An orthodontic bracket according to claim 5 wherein the tooth contact surface of the base portion is treated by one of the group of treatments of shot-peening, ion beam etching, or reactive ion beam etching to increase effective surface area in order to enhance bonding strength to dental enamel.

15. An orthodontic bracket according to claim 5 wherein the tooth contact surface of the base of the bracket is machined to provide undercuts for increasing surface area for better bonding to dental enamel.

16. An orthodontic bracket according to claim 5 wherein the tooth contact surface of the base of the bracket is attached to a mesh for better bonding to dental enamel.

17. An orthodontic bracket according to claim 1 wherein said bracket is made of a material that contains at least 80% metallic titanium by weight in its composition.

18. An orthodontic bracket according to claim 17 wherein said bracket is made of an alloy that contains at least 80% titanium by weight in its composition and addition contains at least one element from the group of Al, V, Fe and Nb.

19. An orthodontic bracket according to claim 1 wherein said bracket is made of a material that contains at least 99% metallic titanium by weight in its composition.

20. An orthodontic bracket according to claim 1 wherein said bracket serves as an active appliance.

* * * * *

UNITED STATES PATENT AND TRADEMARK OFFICE
CERTIFICATE OF CORRECTION

PATENT NO. : 5,232,361
DATED : August 3, 1993
INVENTOR(S) : ROHIT SACHDEVA et al.

It is certified that error appears in the above—identified patent and that said Letters Patent is hereby corrected as shown below:

Col. 8, line 36, please delete "or" and insert
--orthodontic--.

Signed and Sealed this

Fifteenth Day of March, 1994

Attest:

BRUCE LEHMAN

Attesting Officer     Commissioner of Patents and Trademarks